(12) United States Patent
Xie

(10) Patent No.: US 6,585,773 B1
(45) Date of Patent: Jul. 1, 2003

(54) INSERTABLE STENT AND METHODS OF MAKING AND USING SAME

(75) Inventor: Hua Xie, Beaverton, OR (US)

(73) Assignee: Providence Health System-Oregon, Seattle, WA (US)

( * ) Notice: Subject to any disclaimer, the term of this patent is extended or adjusted under 35 U.S.C. 154(b) by 0 days.

(21) Appl. No.: 09/763,304

(22) PCT Filed: Aug. 18, 1999

(86) PCT No.: PCT/US99/19003

§ 371 (c)(1),
(2), (4) Date: Feb. 20, 2001

(87) PCT Pub. No.: WO00/10488

PCT Pub. Date: Mar. 2, 2000

Related U.S. Application Data

(60) Provisional application No. 60/097,357, filed on Aug. 21, 1998.

(51) Int. Cl.$^7$ .................................................. A61F 2/04
(52) U.S. Cl. ........................ 623/23.7; 606/213; 606/214
(58) Field of Search ................................ 623/925, 23.7, 623/23.72, 23.75, 1.47, 1.48; 606/213, 214

(56) References Cited

U.S. PATENT DOCUMENTS

| | | | |
|---|---|---|---|
| 4,705,039 A | * 11/1987 | Sakaguchi et al. .......... 128/334 |
| 5,141,516 A | 8/1992 | Detweiler | |
| 5,180,392 A | * 1/1993 | Skeie et al. .................... 623/11 |
| 5,192,289 A | 3/1993 | Jessen | |
| 5,209,776 A | 5/1993 | Bass et al. | |
| 5,292,362 A | 3/1994 | Bass et al. | |
| 5,306,286 A | 4/1994 | Stack et al. | |
| 5,425,739 A | 6/1995 | Jessen | |
| 5,510,077 A | 4/1996 | Dinh et al. | |
| 5,527,337 A | 6/1996 | Stack et al. | |
| 5,549,122 A | 8/1996 | Detweiler | |
| 5,593,403 A | 1/1997 | Buscemi | |
| 5,659,400 A | 8/1997 | Edakubo et al. | |
| 5,749,895 A | * 5/1998 | Sawyer et al. ............... 606/214 |
| 5,762,625 A | 6/1998 | Igaki | |
| 5,769,883 A | 6/1998 | Buscemi et al. | |
| 5,776,184 A | 7/1998 | Tuch | |
| 5,849,035 A | 12/1998 | Pathak et al. | |
| 5,851,231 A | 12/1998 | Wolff et al. | |
| 5,989,244 A | * 11/1999 | Gregory et al. ................. 606/8 |

* cited by examiner

Primary Examiner—David H. Willse
Assistant Examiner—Jamie S. Blanco
(74) Attorney, Agent, or Firm—Marger Johnson & McCollom, P.C.

(57) ABSTRACT

An insertable stent is provided for joining together and facilitating healing of adjacent tissues. Typically, the tissues are mammalian tissues. The insertable stent is made from completely non-toxic, bio- and blood-compatible materials. Each of the tissues employed herein defines an internal cavity. The insertable stent body defines a bore. The bore permits fluid to pass through the insertable stent body. In use, the insertable stent body is introduced into the internal cavities of the tissues. The insertable stent body fits within the confines of, and in contact with, each of the adjacent tissues. Typically, at least a portion of the insertable stent body is fusible to the adjacent tissues for facilitating healing of these tissues.

46 Claims, 4 Drawing Sheets

INSERTABLE STENT AND METHODS OF MAKING AND USING SAME

This application claims the benefit of Provisional Application No. 60/097,357, filed Aug. 21, 1998.

This invention was made with Government support under Grant No. DAMD17-96-1-6006 awarded by U.S. Army Medical Research Acquisition Activity. The U.S. Government has certain rights in the invention.

BACKGROUND OF THE INVENTION

The present invention relates to stent technology. Advances of laser tissue welding in urinary tract repair are able to provide a rapid watertight seal and avoid potential lithogenesis caused by conventional sutures and staples. However, some problems have limited the clinical use of this technology, such as unreliable fusion strength, thermal damage of welded tissue and lack of a standard reference endpoint during welding procedures.

In U.S. Pat. No. 5,549,122, a method and apparatus for molding polymeric structures in vivo is disclosed. The structures comprise polymers that may be heated to their molding temperature by absorption of visible or near-visible wavelengths of light. By providing a light source that produces radiation of the wavelength absorbed by the polymeric material, the material may be selectively heated and shaped in vivo without a corresponding heating of adjacent tissues or fluids to unacceptable levels. The apparatus comprises a catheter having a shaping element positioned near its distal end. An emitter provided with light from at least one optical fiber is positioned within the shaping element. The emitter serves to provide a moldable polymeric article positioned on the shaping element with a substantially uniform light field, thereby allowing the article to be heated and molded at a desired treatment site in a body lumen.

In U.S. Pat. No. 5,141,516, a dissolvable anastomosis stent comprises a first member for receiving a first vessel stump, a second member for receiving a second vessel stump, and engaging means for engaging the first and second members where the engaging means and members are constructed of a biocompatible, non-toxic material which substantially completely dissolves mammalian bodily fluids. In addition, methods for preparing the dissolvable anastomosis stent and methods for surgical mammalian anastomoses using the dissolvable anastomosis stent are disclosed.

In U.S. Pat. No. 5,306,286, an absorbable stent for placement at the locus of a stenotic lesion which is flexible and compliance for safe and effective delivery to the cite of a coronary obstruction, for example, and so as to avoid arterial rupture or aneurysm formation while under continuous stress of a beating heart. The stent is expandable from a reduced diameter configuration, which facilitates delivery to the cite of a targeted arterial obstruction, to an expanded configuration when disposed within the targeted area The stent can be carried to the cite to be treated and expanded to its supporting diameter on any suitable expandable catheter such as a mechanically expandable catheter or a catheter having an inflatable balloon. The stent is formed so as to have a wall with pores and/or holes to facilitate tissue ingrowth and encapsulation of the stent. The stent will subsequently be bioabsorbed to minimize the likelihood of embolization of the dissolved material.

In U.S. Pat. No. 5,192,289, a stent or support is disclosed for use in the connection or anastomosis of severed vessels to support and seal the anastomotic site. The stent includes substantially cylindrical sections separated by a tapered transitional region. The cylindrical sections are provided with flanges that define tapered sealing surfaces. The dimensions of the two sections are selected to correspond with the diameter of the portions of the vessel to be supported. The stent is preferably made of polyglycolic acid and the dimensions of the stent are selected to provide optimal support and sealing characteristics with a minimum of damage to the epithelial lining of the vas deferens. In two preferred applications, the stent is used in anastomosis of the severed ends of a vas deferens and a Fallopian tube. A gauge is used to measure the severed ends and, in that manner, determine the appropriate dimensions of the stent.

In U.S. Pat. No. 5,425,739, a stent or support is disclosed for use in the connection or anastomosis of severed vessels to support and seal the anastomotic site. The stent includes substantially cylindrical sections separated by a tapered transitional region. The cylindrical sections are provided with flanges that define tapered sealing surfaces. The dimensions of the two sections are selected to correspond with the diameter of the portions of the vessel to be supported. The stent is preferably made of polyglycolic acid and the dimensions of the stent are selected to provide optimal support and sealing characteristics with a minimum of damage to the epithelial lining of the vas deferens. In three preferred applications, the stent is used in anastomosis of the severed ends of a vas deferens, a Fallopian tube, and a blood vessel. A gauge is used to measure the severed ends and, in that manner, determine the appropriate dimensions of the stent. A technique of forming porous stents, and other structures, is also disclosed.

In U.S. Pat. No. 5,662,712, a method and apparatus for molding polymeric structures in vivo is disclosed. The structures comprise polymers that may be heated to their molding temperature by absorption of visible or near-visible wavelengths of light. By providing a light source that produces radiation of the wavelength absorbed by the polymeric material, the material may be selectively heated and shaped in vivo without a corresponding heating of adjacent tissues or fluids to unacceptable levels. The apparatus comprises a catheter having a shaping element positioned near its distal end. An emitter provided with light from at least one optical fiber is positioned within the shaping element. The emitter serves to provide a moldable polymeric article positioned on the shaping element with a substantially uniform light field, thereby In U.S. Pat. No. 5,762,625, a luminal stent inserted and fixed in a vessel, such as a blood vessel, so as to maintain the shape of the vessel, and a device for inserting and fixing the luminal stent, are disclosed. The luminal stent is formed of a yarn of bioabsorbable polymer fibers, which yarn is shaped in a non-woven non-knitted state in, for example, a meandering state, around the peripheral surface of an imaginary tubular member. The bioabsorbable polymer includes polylactic acid, polyglycol acid, polyglactin, polydioxanone, polyglyconate, polyglycol acid and a polylactic acid-.epsilon.-caprolactone copolymer. The device for inserting and fixing the luminal stent consists in a catheter having a balloon-forming portion in the vicinity of a distal end thereof and the luminal stent fitted on the balloon-forming portion and affixed to the balloon-forming portion by a bio-compatible material, such as an in vivo decomposable polymer, such as polylactic acid, water-soluble protein or fibrin sizing agent.

In U.S. Pat. No. 5,292,362, a composition is disclosed for bonding separated tissues together or for coating tissues or prosthetic materials including at least one natural or synthetic peptide and at least one support material which may be activated by energy and to methods of making and using the same.

In U.S. Pat. No. 5,527,337, a bioabsorbable stent is provided for placement at the locus of a stenotic portion of a body passage, such as a blood vessel, which is flexible and compliant for safe and effective delivery to the site of the stenotic portion of, for example, a blood vessel, and so as to avoid the disadvantages of chronic implantation, such as arterial rupture or aneurism formation while exposed to the continuous stresses of a beating heart. The stent is formed from a bioabsorbable material and is porous or has apertures defined there through to facilitate tissue ingrowth and encapsulation of the stent. The stent is encapsulated and biodegrades or bioabsorbs within a period of days, weeks or months as desired following encapsulation to thereby minimize the likelihood of embolization or other risks of the dissolved material and to avoid the disadvantages of chronic implantation.

In U.S. Pat. No. 5,209,776, a tissue bonding and sealing composition and method of using the same is provided. Disclosed is a composition for bonding separated tissues together or for coating tissues or prosthetic materials including at least one natural or synthetic peptide and at least one support material which may be activated by energy.

In U.S. Pat. No. 5,510,077, an intraluminal stent comprising fibrin treatment of restenosis is provided by a two stage molding process.

In U.S. Pat. No. 5,776,184, a device for delivery of a therapeutic substance into a body lumen including a polymer in intimate contact with a drug on a stent allows the drug to be retained on the stent during expansion of the stent and also controls the administration of drug following implantation. The adhesion of the coating and the rate at which the drug is delivered can be controlled by the selection of an appropriate bioabsorbable or biostable polymer and the ratio of drug to polymer.

In U.S. Pat. No. 5,659,400, a method for making an intravascular stent by applying to the body of a stent a solution which includes a solvent, a polymer dissolved in the solvent and a therapeutic substance dispersed in the solvent and then evaporating the solvent. The inclusion of a polymer in intimate contact with a drug on the stent allows the drug to be retained on the stent during expansion of the stent and also controls the administration of drug following implantation. The adhesion of the coating and the rate at which the drug is delivered can be controlled by the selection of an appropriate bioabsorbable or biostable polymer and the ratio of drug to polymer in the solution. By this method, drugs such as dexamethasone can be applied to a stent, retained on a stent during expansion of the stent and elute at a controlled rate.

During the past decade, the application of laser solders has greatly increased the bonding strength of laser fusion. Human albumin as a suitable solder agent were applied in several tissue welding such as urethra, ureters, skin and vascular due to its high safety. Several studies have demonstrated that the welding strength of laser tissue soldering depended on solder protein concentration. But, the technical problem still remains is the precise seromuscular apposition of tubular organs for accurate placement of the laser spot and uniform layering of the solder on the fusion surface during laser welding procedures. Those problems could cause fusion strength unreliable, wound healing process prolonged and increased scar tissue at anastomotic site so that anastomosis failed.

SUMMARY OF THE INVENTION

An insertable stent is provided for joining together and facilitating healing of adjacent tissues. Typically, the tissues are human tissues. Preferably, the insertable stent is made from completely non-toxic, bio- and blood-compatible materials, which are abstracted from the native serum and tissue of mammalian.

Each of the tissues employed herein defines an internal cavity. More preferably, the insertable stent comprises an insertable stent body which defines a bore. The bore permits fluid to pass through the insertable stent body.

In use, the insertable stent body is introduced into the internal cavities of the tissues. The insertable stent body fits within the confines of, and in contact with, each of the adjacent tissues. Most preferably, at least a portion of the insertable stent body is fusible to the adjacent tissues for facilitating healing of these tissues.

The preferred insertable stent of this invention is different than previous products in that it is made from mammalian serum and tissue, which is completely non-toxic, bio- and blood compatible, and is therefore substantially dissolvable. More specifically, during the healing process, at least a portion of the insertable stent body can be dissolved. Preferably, the insertable stent comprises a biocompatable insertable stent body.

The insertable stent body preferably includes chromophores such photothermal dye materials for absorbing electromagnetic radiation. The stent typically plays support, alignment, and soldering roles in the photothermal welding anastomosis processes. Thus photothermal welding is simplified and quickened, and the strength of welding is reinforced using the insertable stent. Suitable chormophoric dyes comprise indocyanine green, methylene blue, flourescein, and india ink, Prussian blue, copper phthalocyanine, eosins, acridine, iron oxide, jenner stain, and acramine yellow.

The insertable stent body preferably includes at least one therapeutic drug. Examples of such drugs are; antibiotics such as penicillin, ampiciline, and gentamycin; antiinflammatories such as glucocorticoids, dexamethasone; antithombotics such as heparain; vitamins and peptide growth factors such as epithelial growth factor and transforming growth factor; nerve growth factors, and insulin like growth factors.

The insertable stent body can preferably comprise a protein. For example, the insertable stent body can comprise any one or more of the following proteins: albumin, elastin, collagen, globulin, fibrinogen, fibronectin, thrombin, polypeptides, and fibrins. The insertable stent body can also comprise a carbohydrate, typically a sugar.

The insertable stent body preferably includes a radiopaque agent for preventing passage of x-rays or other radiation. Examples of such agents are; iothalamate meglumine, diatrizoate meglumine, diatrizoate sodium, and ioversol.

Furthermore, a method can also be provided for manufacturing an insertable stent for joining together and facilitating healing of adjacent tissues. The method preferably comprises first forming the insertable stent body and then forming a bore therewith for permitting fluid to pass therethrough.

In addition, a method is provided for using the insertable stent to join together and facilitate healing of the adjacent tissues. The method preferably comprises providing a plurality of tissues, each having an internal cavity and ends. Then, the above described insertable stent is introduced into the cavity of each tissue. Finally, the tissues are aligned so that the ends are located adjacent to each other, and the insertable stent body is fused to the tissues. In another embodiment of the invention, the tissues are fused to each other.

The step of fusing the insertable stent body to the adjacent tissues preferably comprises electromagnetically radiating the insertable stent body, which most preferably comprises a photothermal dye such as described above. After the fusing step is completed, preferably, the insertable stent body generally comprises at least one fused portion and at least one unfused portion. The method preferably includes the step of dissolving at least a portion of the unfused portion of the insertable stent body during healing of the tissues. More specifically, the insertable stent could be photothermally sensitive which allows it to absorb a range of wavelengths of a light source that produces a heat denatured reaction to coagulate and bind tissues at irradiation site, and which depends on what chromophores are added. The stent can produce heat denatured coagulation reaction by other energy sources. The stent is preferably designed so that the non-denatured portion is dissolved in body fluid in several minutes, and the denatured portion adheres to a bond site to form a seal circular ring to seal and support the vessel anastomosis site so that be it will be biodegradable during the healing process.

An insertable stent can be made from a mammalian serum and/or a tissue source which comprises hydrolyzable protein that is a group of non-toxic, bio- and blood-compatible natural material. The insertable stent, including chromophores, plays a significant support role in the vessel intralumen and plays a soldering role in the energy welding processes. The non-denatured portion of the stent is typically dissolved in body fluid after energy welding anastomosis as so to not effect the vessel fluid flow and to be biodegradable.

The insertable stent can be used for temporal connection and supporting vessels during anastomosois processes. The anastomostic techniques are conventionally those such as suturing, stapling, gluing and energy welding processes.

The insertable stent with chromophores which is a photothermal sensitive insertable stent will be used for temporal connection and supporting vessels during end to end anastomosis techniques which comprise several sutureless vessel anastomosis techniques using energy welding to produce heat coagulation effect. The anastomostic techniques consist of conventional suturing, stapling, gluing and energy welding processes.

The stent will be as a drugs carrier to increase local drug concentration in the intraluminal of vessel for therapeutic and preventing the surgical complication as wound healing delayed, stricture of anastomosis and/or diseases. The method can also include the step of releasing at least a portion of the therapeutic drug from the insertable stent body. This will assist with the healing of the tissues.

The tissues are preferably selected from a group consisting of blood vessels, gastrointestinal, genitourinary, reproductive, respiratory tubes, grafts, and synthetic prosthetics. At least one of the tissues will preferably expand when the insertable stent is introduced into the cavity.

The fusing preferably comprises photothermal bonding such as laser welding. The fusing can also comprise thermal bonding facilitated by bipolar electrodes or magnetic and microwave thermal welding. The fusing can also comprise chemical bonding without an energy source which is extrinsic to the tissues, such as with biocompatable sealants. Examples of such sealants are cyanoacrylate glue and fibrin glue. The fusing can also comprise photochemical bonding, such as riboflavin fusion.

DETAILED DESCRIPTION OF PREFERRED EMBODIMENTS

Figure 1:
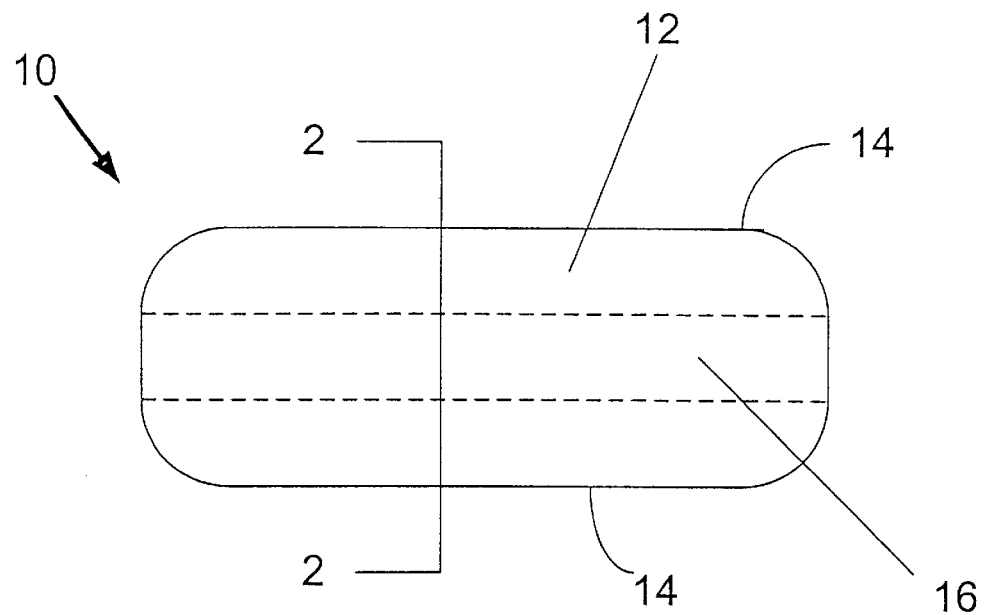
FIG. 1 is schematic view of the insertable stent according to the present invention.
Figure 2:
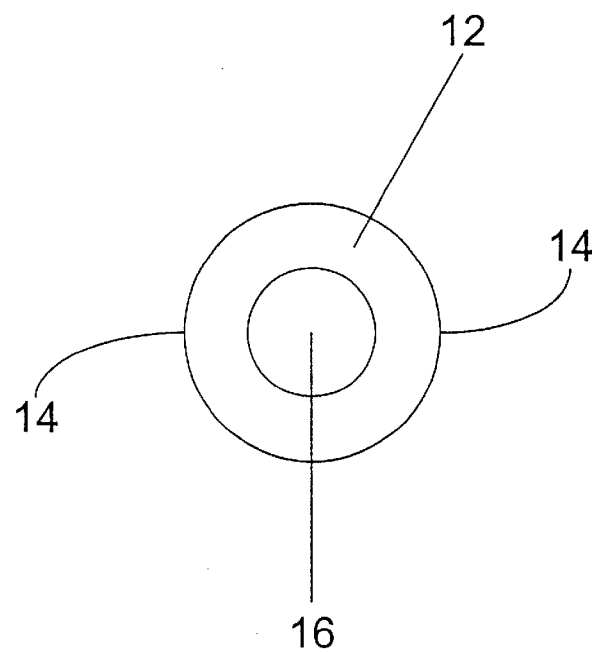
FIG. 2 is an end view taken along line 2—2 in FIG. 1.
Figure 3:
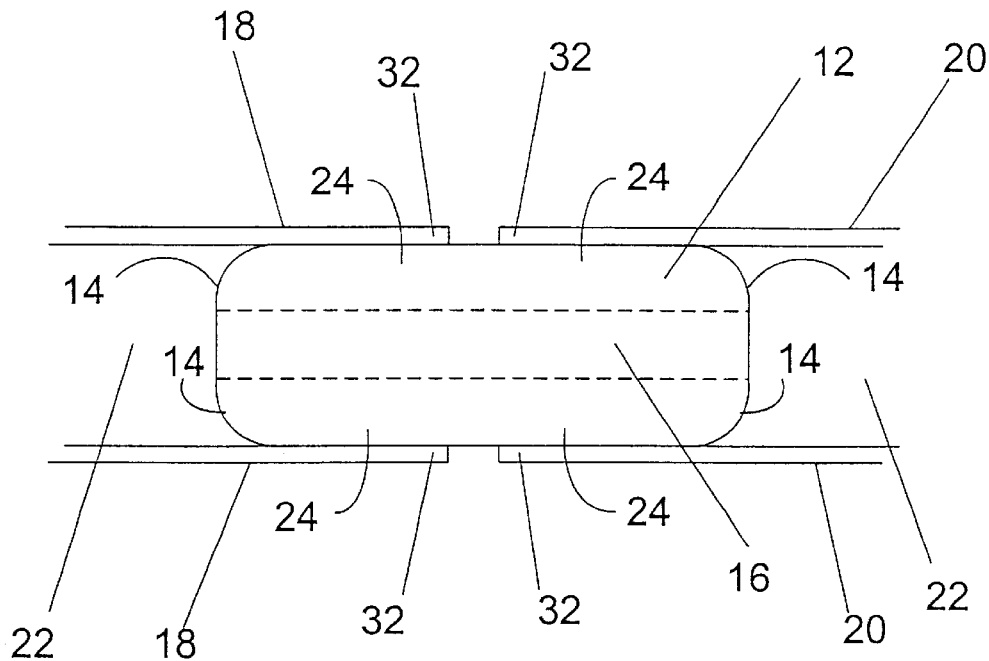
FIG. 3 is a schematic view showing the insertable stent immediately after introduction into tissue cavity in accordance with the present invention.

Referring to the drawings, there is shown in FIGS. 1 and 2 an insertable stent 10 in accordance with the present invention. The insertable stent 10 comprises an insertable stent body 12 having an outer surface 14. The insertable stent body 12 defines a bore 16 for permitting fluid to pass therethrough. In the preferred embodiment, the insertable stent body 12 is formed from a material that dissolves in bodily fluids, is non-toxic, and causes little or no inflammation in the tissues during the healing process. Most preferably, an insertable stent body 12 formed from human serum albumin is used. FIGS. 3–6 shows the preferred technique for using the insertable stent body to join together and facilitate healing of adjacent tissues. As depicted in FIG. 3, the insertable stent body 12 is inserted into tissue cavities 22 defined by a first tissue 18 and second tissue 20. The tissues have tissue ends 32. Once inserted into the cavities 22, the outer surface 14 is in contact with both first tissue 18 and second tissue 20. In one aspect of the invention, the insertable stent body 12 stretches and expands the tissues when it is inserted therein.

Figure 4:
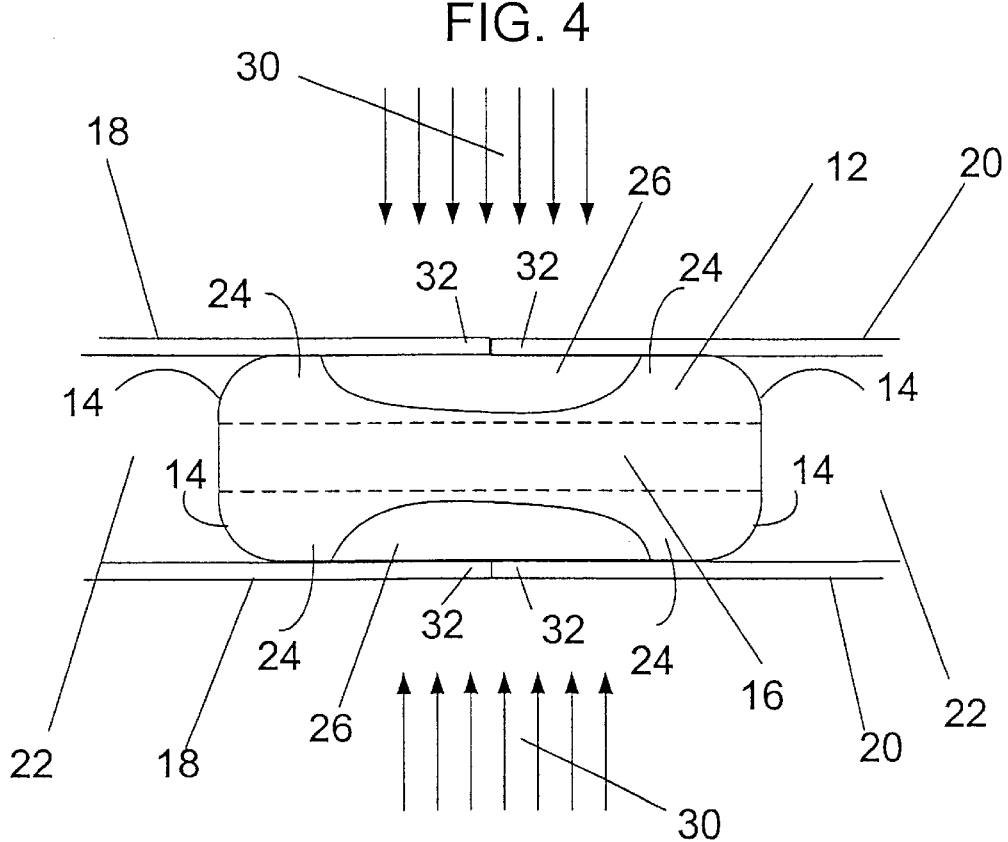
FIG. 4 is a schematic view during the fusing procedure in accordance with the present invention.
Figure 6:
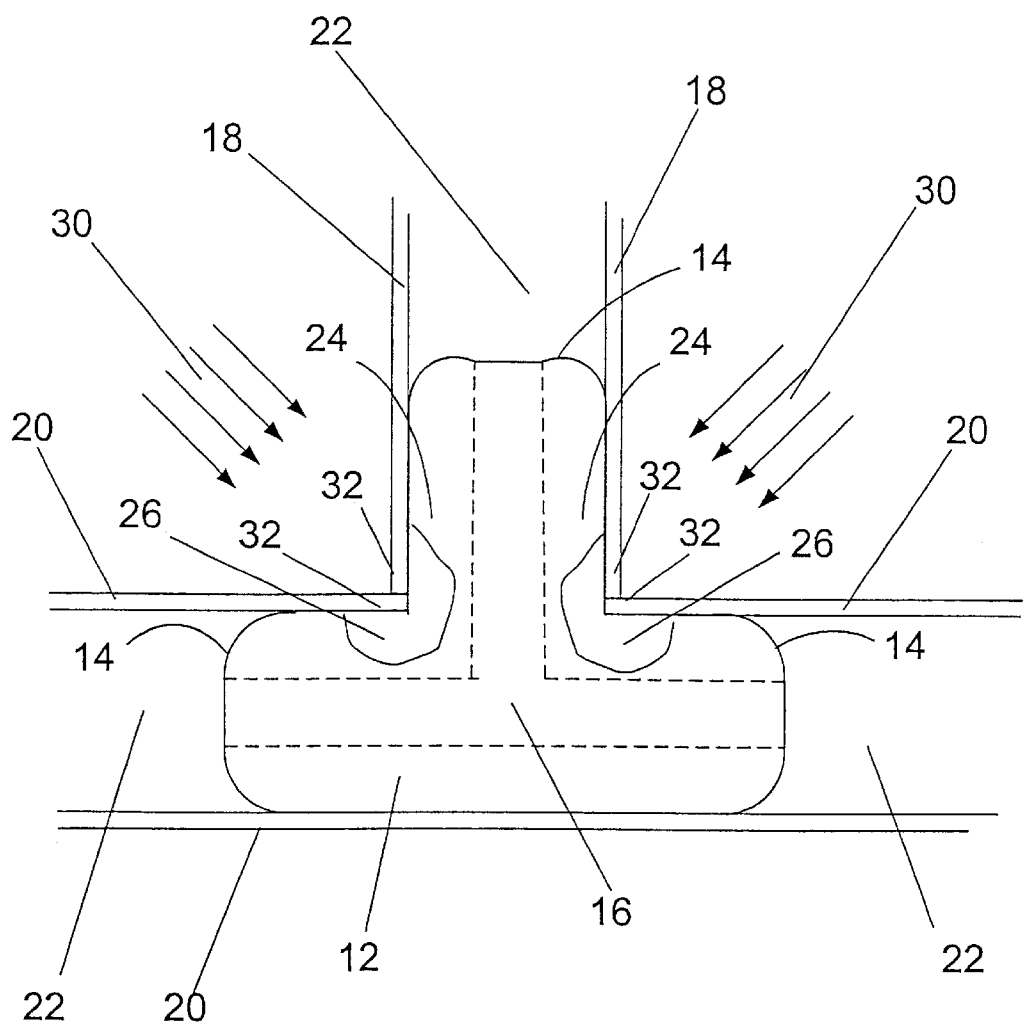
FIG. 6 is a schematic view during the fusing procedure in accordance with the present invention.

In the preferred embodiment, the insertable stent body 12 comprises a fusible chromophore-containing insertable stent body portion 24. The fusible dyed insertable stent body portion 24 comprises an energy absorbing material such as a chormophore, preferably, a photothermal dye such as indocyanine green. After the insertable stent is inserted into the tissue cavities 22, the tissue ends 32 are aligned so that they are adjacent to each other as shown in FIGS. 4 and 6. Next, electromagnetic radiation 30 is directed at the fusible dyed insertable stent body portion 24. Preferably, the electromagnetic radiation 30 has a wavelength that is not absorbed by the tissues, but that will fuse the insertable stent body 12 to the tissues. Most preferably, the electromagnetic radiation 30 has a wavelength of about 800 nm. The electromagnetic radiation 30 directed at the fusible dyed insertable stent body portion 24 is absorbed by the dye and converted into thermal energy. The thermal energy causes the radiated portion of the fusible dyed insertable stent body portion 24 to fuse to the tissues, thus forming the fused insertable stent body-tissue portion 26.

Advantageously, the energy source is an electromagnetic energy source, such as a laser, and the absorbing agent is a dye having an absorption peak at a wavelength corresponding to that of the laser. The biomaterial and the tissue to be welded have much less absorption of light at this wavelength and the effect therefore is confined to a zone around the dyelayer. A preferred energy source is a laser diode having a dominant wavelength at about 808 nm and a preferred dye is indocyanine green (ICG), maximum absorbance 795–805 nm. Other laser/dye combinations can also be used. It is preferred that the dye be incorporated in the insertable stent body portion 24. The dye can also be applied to the surface of the body portion 24 is to be welded or secured to the tissue. The dye can be applied directly to the body portion 24 or the surface of the body portion 24 can first be treated or coated (eg primed) with a composition that controls absorption of the dye into thereinto so that the dye is kept as a discrete layer or coating.

Alternatively, the dye can be bound to the body portion 24 so that it is secured to the surface and prevented from leeching into the material. The dye can be applied in the form of a solution or the dye can be dissolved in or suspended in a medium which then can be applied as a thin sheet or film, preferably, of uniform thickness and dye concentration.

Figure 5:
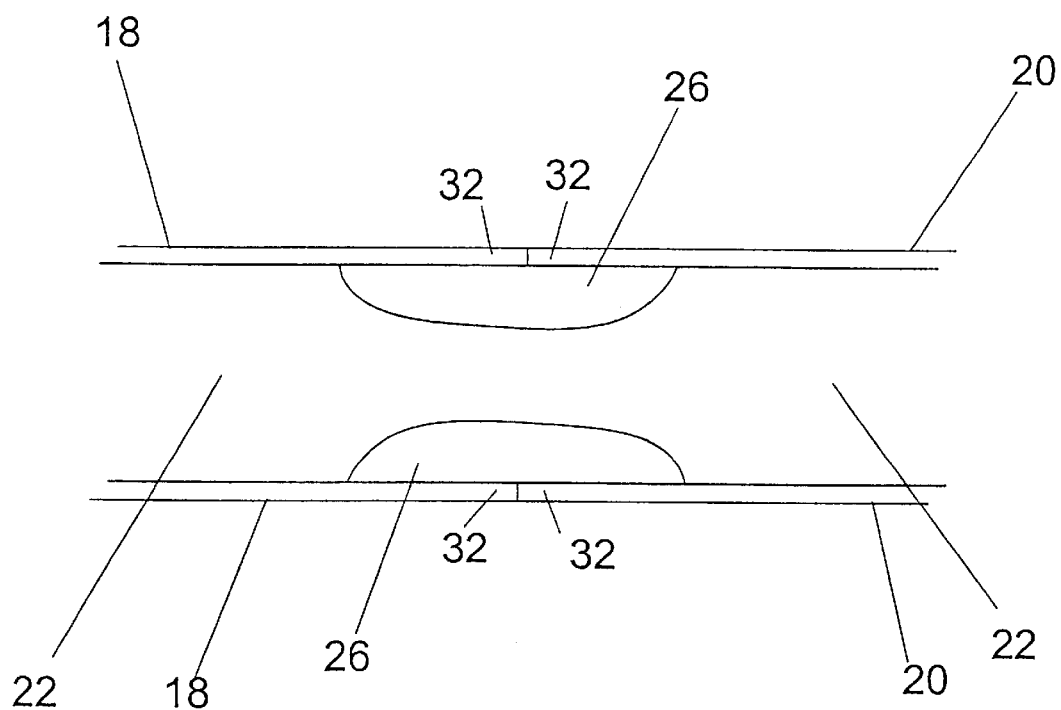
FIG. 5 is a schematic view after fusing and dissolving, and during healing of the tissues in accordance with the present invention.

In the preferred embodiment, once the fused insertable stent body-tissue portion 26 has been formed, the remainder of the insertable stent body 12 is dissolved away by the human bodily fluids passed through the bore 16. As shown in FIG. 5, the fused insertable stent body-tissue portion 26 bonds the tissue ends 32 together and forms a liquid tight seal during healing of the tissues.

EXAMPLE 1

Sutureless End to End Ureteral and Heterograft Anastomosis—In Vitro Study

Preparation of PSH Stent and Solder

25% Human serum albumin (MW: 66,500, Michigan Dept. of Public Health, U.S. license No.99, MI) was filtered through an ultrafilter membrane (YM 30, Amicon) using the ultrafiltration system (Model 8400, Amicon, MA) to concentrate it to 50% (W./V.). 10 mM ICG (Sigma, I2633, MO) solution was filtered for sterilization (Gameo 25ES, Fisher) and added to 50% albumin at 1:100 by volume and mixed well for 3 min. The mixture was air blow until the solvent evaporated and became moldable. The moldable albumin was molded to a hollow stent with outer diameter of 3.5 mm, inner diameter of 2.0 mm and 1.5 cm in length. The stent was stored at about $-4°$ C. in the dark until use. The procedure was performed using sterile techniques. The liquid solder was made of 50% (W./V.) albumin with 0.1 mM ICG that was made similar to the photothermal sensitive stent without drying procedures. The solder was stored in a 1 ml syringe at $-4°$ C. in the dark until use.

Elastin Based Heterograft

The elastin based heterograft was processed from freshly harvested porcine carotid arteries. The vessels were decellularized and digested by 1% triton-X 100, DNase and collagenase. The final product was composed of elastin at lumen surface and collagen on the outer surface, and each graft was 6 cm in length, 3–4 mm in inside diameter and 1 mm thick.

Laser System

Laser treatments were performed with a diode laser module (Diomed Limited, Cambridge, UK) coupled to a quartz silica non-contact fiber optic (600 $\mu$m diameter). The laser system consists of a phased array of gallium-aluminum-arsenide semiconductor diodes, and the major wavelength output of the diode laser is 808 nm. In aiming beam allow the operator to visualize the spot size of the laser during activation. The spot diameter was ~1 mm at a distance of ~2 mm. Laser power was measured and recorded at the out of the optic fiber with a built-in laser meter monitor. The maximum diode power output is 25 W. The laser was used in continuous wave mode with 1 W output.

Fresh ureter segments were harvested from domestic swine with minimal trauma and immediately placed in sterile 0.9% saline solution at $-4°$ C. Elastin based heterograft was provided by our biomaterial research laboratory.

The study was divided into three groups. In group 1, 12 ureters were completely transected and were reanastomosed end to end using PSH stent laser fusion. In group 2, 12 ureters were anastomosed to the elastin based heterograft using PSH stent laser fusion and in group 3, 17 ureter to heterograft anastomosis were using laser liquid solder technique. Each ureter or elastin based heterograft was carefully placed over and tied on a stainless steel tube with 1-0 silk tie to prevent sliding. The stainless steel tube was connected in parallel to an infusion pump (Syringe infusion pump 22, Harvard apparatus, MA) and pressure recorder (Pressure Monitor 4, Living System Instrumentation, VT). The ureters and heterograft stumps were spatulated and opposed using two 6-0 vicyl sutures. During PSH stent laser welding, the two ends were pulled over the PSH Stent to approximate in an end to end fashion. While working on liquid solder welding, the ureter and heterograft ends were pulled over a 3.5 mm OD. balloon catheter for end to end apposition. The solder was applied in a thin coat on the seam before laser welding. The solder covered approximately 1 mm on each side of the anastomosis. The holding suture material melted away with laser welding. The samples were treated for burst pressure and tensile strength testing.

A perfusion system was set up between the welded vessel and infusion pump for burst pressure testing. A 0.9% NaCl with 1% methylene blue solution was infused at 2 ml/min flow rate to dissolve the PSH stent and check up for leaks of anastomotic site. After the stent was dissolved, the pressure recorder switch was turned on to record welding burst pressure. The expandable balloon catheter was deflated and removed carefully from welded vessel using laser welding.

The vessels were perfused for an hour and then the burst pressure (mmHg) was recorded. While the vessel didn't break during the burst pressure testing were sent for histological examination.

The welded vessels were soaked in 37° C. saline solution overnight after welding and then tested for tensile strength. The breaking force of the laser weld was recorded using a tension tester (Vitrodyne V1000, Liveco, VT). The standard load weight was 5000 g.

In groups 1 and 2, all samples were divided into 2 sets, one set was tested for burst pressure and the other for tensile strength. In group 3, 8 samples were tested for burst pressure and 9 for tensile strength.

Results

Measurable objective parameters comparing each group were tensile strength, burst pressure and total energy required to complete the anastomosis were studied.

There were significant differences in burst pressures between the grafts welded with the PSH stent and those using the liquid solder. Higher burst pressures were observed in the groups 1 and 2 which used the PSH stent. Some burst pressures were higher than 183 mmHg and most of the measurements could not be recorded because our pressure recorder was calibrated to a maximum pressure of 200 mmHg. Three quarters of the measurements were above 200 mmHg in groups 1 and 2 (9/12). However, in group 3, the burst pressure ranged from 15→200 mmHg. Only 33.3% (3/9) in group 3 were over 200 mmHg. 83.3% (5/6) and 66.7% (4/6) of burst pressure were measured above 200 mmHg in group 1 and group 2, respectably.

The tensile strength of groups 1 and 2, with the PSH stent, were 420 (190 g/cm2 and 370±170 g/cm2, respectively. In the group 3, with the liquid solder, the average of tension was 240±130 g/cm2. These values were significantly different (P<0.05).

The total energy consumption to complete the anastomosis in the both of the PSH stent groups and solder group were significantly different. More energy and time was spent at the anastomosis site using the liquid solder (200±45 J.) as compared with using the PSH Stent (84±38 J) for laser welding. But, there was no significant difference between welding ureter to ureter and ureter to heterograft using the PSH stent.

EXAMPLE 2

Sutureless End to End Ureteral and Heterograft Anastomosis—In Vivo Study

Preparation of PSH Stent and Solder

25% Human serum albumin (MW: 66,500, Michigan Dept. of Public Health, U.S. license No.99, MI) was filtered through an ultrafilter membrane (YM 30, Amicom) using the ultrafiltration system (Model 8400, Amicom, MA) to concentrate it to 50% (W./V.). 10 mM ICG (Sigma, I2633, MO) solution was filtered for sterilization (Gameo 25ES, Fisher) and added to 50% albumin at 1:100 by volume and mixed well for 3 min. The mixture was air blow until the solvent evaporated and became moldable. The moldable albumin was molded to a hollow stent with outer diameter of 3.5 mm, inner diameter of 2.0 mm and 1.5 cm in length. The stent was stored at $-4°$ C. in the dark until use. The procedure was performed using sterile techniques.

The liquid solder was made of 50% (W./V.) albumin with 0.1 mM ICG that was made similar to the photothermal sensitive stent without drying procedures. The solder was stored in a 1 ml syringe at $-4°$ C. in the dark until use.

Elastin Based Heterograft

The elastin based heterograft was processed from freshly harvested porcine carotid arteries. The vessels were decellularized and digested by 1% triton-X 100, DNase and collagenase. The final product was composed of elastin at lumen surface and collagen on the outer surface, and each graft was 6 cm in length, 3–4 mm in inside diameter and 1 mm thick.

Laser System

Laser treatments were performed with a diode laser module (Diomed Limited, Cambridge, UK) coupled to a quartz silica non-contact fiber optic (600 $\mu$m diameter). The laser system consists of a phased array of gallium-aluminum-arsenide semiconductor diodes, and the major wavelength output of the diode laser is 808 nm. In aiming beam allow the operator to visualize the spot size of the laser during activation. The spot diameter was ~1 mm at a distance of ~2 mm. Laser power was measured and recorded at the out of the optic fiber with a built-in laser meter monitor. The maximum diode power output is 25 W. The laser was used in continuous wave mode with 1 W output.

Twelve domestic female swine, weight 30–40 lbs., were studied in this project. Five pigs were used for acute experiments and seven were used for chronic experiments. Our surgical protocol followed guidelines for the care and use of the laboratory animals and was approved by the Animal Care and Use Committee of Oregon Health Sciences University.

The animal was sedated with an IM injection of Telazol 1.5 ml followed by general endotracheal anesthesia, using 1–2% Halothane inhalant. Heart rate and oxygen saturation was monitored during the surgery. The anesthetized pig was positioned supine, and shaved and prepped in a sterile fashion. The paramedian retroperitoneal approach was made from fourth nipple to below the last nipple.

In the acute group (N=5), 6–8 cm of the mid-segment of both ureters were exposed and mobilized in an atraumatic manner, and 3–4 cm were resected. On the right side, two PSH stents were placed into the elastin tubular heterograft on each end with a 4.8 Fr.×18 cm double J ureteral stent inserted through the PSH hollow stent and graft (Circon Surgitek, CA). The double J was placed through free ureteral stumps into renal pelvis above and the bladder below. Then the ureteral stump was pulled over the PSH stent to approximate with the graft. Laser tissue welding was then done on the proximal anastomosis followed by the distal one. On the left side, the ureter was reconstructed with the graft without the PSH stent. The liquid solder was applied in a thin coat on the seam before laser irradiation. The solder covered approximately 1 mm on each side of the anastomosis. The ureter ends and heterografts were spatulated for the anastomosis. One hour after laser welding, retrograde ureterography was preformed, then the animal was sacrificed and the specimen was harvested and tested for tensile strength (Vitrodyna 1000, Liveco, VT).

In the chronic group (N=7), only the right ureter was operated. Two animals were used as controls in this group and end to end ureterureterostomy was done using laser welding with the PSH stent. Five animals were used to perform ureter to heterograft end to end anastomosis using PSH stent and laser. A 12 Fr. urethral catheter was placed through urethra output from bladder. The bladder and abdominal incision were closed in a standard fashion using a running 3-0 chromic suture after making sure no leakage or bleeding was present at the anastomotic sites. The catheter was sutured to the animal's perineal skin and cut short to allow chronic urine drainage and was removed at 1 week after surgery.

The animal was maintained on antibiotics for 14 days (Ampicillin and Getamycin). 1 animals were sacrificed at 1 week, 2 at 2 wk. and 2 at 4 wks. Abdominal X-ray, intravenous pyelography and retrograde ureterography were performed before sacrificed. The double J was removed after retrograde urography. Then ureter was harvested for histology.

The tissue samples were immediately fixed in 10% formalin solution. Then the specimens were embedded with paraffin wax and sliced. Trichrome, VVG, Von Kossas, Actin and H & E staining were performed to study collagen, elastin, calcification and smooth muscle regeneration. Statistical comparisons of all groups within each parameter were examined using single T-test.

Results

The acute experiments were performed in five animals, during which both ureters were replaced partially by elastin based tubular heterograft using the PSH stent on one side and albumin based liquid solder on the other side. Each side had two anastomoses. The table 1 compares the welding time, tensile strength and propensity to leakage during the acute experiments. Welding time for ureter to heterograft anastomosis was significantly (P<0.05) decreased in the PSH stent group (67±27 sec.) compared to the albumin solder group (121±38 sec.). Leakage at the anastomotic sites was interrogated using retrograde ureterography. The liquid albumin soldering had a 30% leak rate (3/10). In the PSH group, there were no immediate leaks evident. No significant difference was found between the both groups in immediate tensile strength.

In the chronic experiment group, one case failed due to anastomotic site leak at one week of postoperatively. Radiographic examination revealed varying degrees of stricture and hydroureteronephrosis in both groups.

The gross and histological examination showed that a solid construct remained the gap between of ureter and heterograft after 1 hour perfusion at the PSH stent laser welding. A sponge construction was observed at liquid solder laser welding. Fibrous tissue surrounding the heterograft and urothelia hyperplasia at anastomosis site were observed at 4 weeks after surgery. At 2 weeks postoperatively, the albumin of the PSH stent plug was degraded and penetrated by fibroblasts. By 4 weeks, the albumin was degraded.

EXAMPLE 3

Laser Fusion of Vascular Heterograft—Acute Study

After proper identification of the animal, anesthesia was induced with Telazole 8 mg/Kg I/M. Isoflurane was given by face mask and the animal was intubated with a size 5 F cuffed endotracheal tube. An I/V was inserted into a vein on its right ear and 7000 units of heparin was given I/V. A six centimeter longitudinal incision was made in the midline of the neck with a #15 blade. Division of the subcutaneous tissue, and fascia between the strap muscles up to the trachea was done using the electrocautery. Next to the trachea on the right side the carotid sheath was identified and the common carotid artery was isolated. The artery was soaked in papaverin solution for five minutes to relieve spasm. The heterograft was washed in heparinized saline for 20 minutes. Vascular clamps were applied on the right common carotid 6 cm apart and the intervening vessel was cut and ends spatulated. A 3.5 mm (outer diameter) albumin-ICG hollow bullet stent was inserted into the heterograft and then was invaginated into the distal carotid stump. Two stay sutures of 7-0 prolene were tied on opposite sides in order to keep the two vessel approximated. Fifty percent albumin-ICG liquid solder was squirted on to the approximated edges and 2 mm on each side. The 805 nm diomed-25 pulsed surgical laser was set at 5 Watts with 0.1 sec pulse width and a 0.2 sec pulse interval. The edges were lased circumferentially. A similar procedure was done on the proximal end of the vessel. The vascular clamps were removed and the graft was perfused for one hour. It took approximately 20 minutes for the bullet to dissolve. The specimen was explanted and sent for histopathology. The animal was sacrificed.

EXAMPLE 4

Laser Fusion of Vascular Heterograft—Acute Study

After proper identification of the animal, anesthesia was induced with Telazole 8 mg/Kg I/M. Isoflurane was given by face mask and the animal was intubated with a size 5 F cuffed endotracheal tube. An I/V was inserted into a vein on its right ear and 7000 units of heparin was given I/V. A six centimeter longitudinal incision was made in the midline of the neck with a #15 blade. Division of the subcutaneous tissue, and fascia between the strap muscles up to the trachea was done using the electrocautery. Next to the trachea on the right side the carotid sheath was identified and the common carotid artery was isolated. The artery was soaked in papaverin solution for five minutes to relieve spasm. The heterograft was washed in heparinized saline for 20 minutes. Vascular clamps were applied on the right common carotid 6 cm apart and the intervening vessel was cut and ends spatulated. A 3.5 mm (outer diameter) albumin-ICG hollow bullet stent was inserted into the heterograft and then was invaginated into the distal carotid stump. Two stay sutures of 7-0 prolene were tied on opposite sides in order to keep the two vessel approximated. Fifty percent albumin-ICG liquid solder was squirted on to the approximated edges and 2 mm on each side. The 805 nm diomed-25 pulsed surgical laser was set at 5 Watts with 0.1 sec pulse width and a 0.1 sec pulse interval. The edges were lased circumferentially. A similar procedure was done on the proximal end of the vessel. The vascular clamps were removed and the graft was perfused for three hour. It took approximately 20 minutes for the bullet to dissolve. The specimen was explanted and sent for histopathology. The animal was sacrificed.

What is claimed is:

1. An insertable stent for joining together and facilitating healing of adjacent tissues, the tissues defining an internal cavity, the insertable stent comprising an insertable stent body including at least one fusible portion, and at least one unfusible portion having a portion which is dissolvable during healing permitting fluid to pass therethrough, the insertable stent body being introduceable into, and fitting within the confines of the internal cavity, in contact with and fusible to the adjacent tissues.

2. The insertable stent of claim 1, which defines a bore therewithin for permitting fluid to pass therethrough.

3. The insertable stent of claim 1, wherein the insertable stent body comprises a biocompatable insertable stent body.

4. The insertable stent of claim 1, wherein the insertable stent body includes a chromophore in the fusible portion.

5. The insertable stent of claim 4, wherein said chromophore comprises a dye material.

6. The insertable stent of claim 1, wherein the insertable stent body includes at least one therapeutic drug.

7. The insertable stent of claim 6, wherein said therapeutic drug is selected from the group consisting of antibiotics, antiinflammatories, antithrombotics, vitamins, peptide growth factors.

8. The insertable stent of claim 1, wherein the insertable stent body comprises a protein.

9. The insertable stent of claim 8, wherein said protein is selected from the group consisting of albumins, elastins, collagens, globulins, fibrinogens, fibronectins, thrombins, and fibrins.

10. The insertable stent of claim 1, wherein the fusible portion of the insertable stent is formed employing an energy source.

11. The insertable stent of claim 10, wherein said energy source is electromagnetic, photothermal or photochemical.

12. The insertable stent of claim 1, wherein the insertable stent body includes a radiopaque agent.

13. The insertable stent of claim 12, wherein said radiopaque agent is selected from the group consisting of iothalamate meglumine, diatrizoate meglumine, diatrizoate sodium, and ioversol.

14. A method for manufacturing an insertable stent for joining together and facilitating healing of adjacent tissues, the tissues defining an internal cavity, comprising:

forming an insertable stent body including at least one fusible portion, and at least one unfusible portion having a portion which is dissovable during healing permitting fluid to pass therethrough, the insertable stent body being introduceable into, and fitting within the confines of the internal cavity, in contact with and fusible to the adjacent tissues.

15. The method of claim 14, wherein the insertable stent body defines a bore therewithin for permitting fluid to pass therethrough.

16. The method of claim 14, wherein said insertable stent body is a biocompatable insertable stent body.

17. The method of claim 14, which includes incorporating at least one chromophore into said insertable stent body in the fusible portion.

18. The method of claim 17, wherein said chromophore is a dye material.

19. The method of claim 14, which includes incorporating at least one therapeutic drug into said insertable stent body.

20. The method of claims 19, wherein said therapeutic drug is selected from the group consisting of antibiotics, antiinflammatories, antithrombotics, vitamins, peptide growth factors.

21. The method of claim 14, wherein the insertable stent body comprises a protein.

22. The method of claim 21, wherein said protein is selected from the group consisting of albumins, elastins, collagens, globulins, fibrinogens, fibronectins, thrombins and fibrins.

23. The method of claim 14, wherein the fusible portion of the insertable stent is formed employing an enery source.

24. The method of claim 23, wherein said energy source is electromagnetic, photothermal or photochemical.

25. The method of claim 14, wherein the insertable stent body comprises a radiopaque agent.

26. The method of claim 25, wherein said radiopaque agent is selected from the group consisting of iothalamate meglumine, diatrizoate meglumine, diatrizoate sodium, and ioversol.

27. A method for joining together and facilitating healing of tissues, comprising:
providing a plurality of tissues each having an internal cavity and ends;
providing an insertable stent comprising a insertable stent body including at least one fusible portion, and at least one unfusible portion having a portion which is dissolvable during said healing;
introducing said insertable stent into the internal cavity of each tissue;
aligning the tissues so that the ends are located adjacent to each other; and
fusing said fusible portion of said insertable stent body to said tissues.

28. The method of claim 27, wherein said unfusible portion defines a bore therewithin for permitting fluid to pass therethrough.

29. The method of claim 27, wherein the insertable stent body comprises a biocompatable insertable stent body.

30. The method of claim 27, wherein the insertable stent body includes a chromophore in the fusible portion.

31. The method of claim 30, wherein said chromophore is a dye material.

32. The method of claim 27, wherein said insertable stent body comprises a protein.

33. The method of claim 32, wherein said protein is selected from the group consisting of alburins, elastins, collagens, globulins, fibrinogens, fibronectins, thrombins and fibrins.

34. The method of claim 27, wherein said insertable stent body, upon fusing, comprises a denatured portion and a non-denatured portion.

35. The method of claim 27, wherein said fusing of insertable stent body to tissues comprises electromagnetically radiating said insertable stent body.

36. The method of claim 27, wherein said insertable stent body comprises at least one fused and at least one unfused portion; and
which includes the step of dissolving at least a portion of the unfused portion of said insertable stent body during healing of said tissues.

37. The method of claim 27, wherein the insertable stent body includes at least one therapeutic drug; and
which includes the step of releasing at least a portion of said therapeutic drug from the insertable stent body during healing of said tissues.

38. The method of claim 37, wherein said therapeutic drug is selected from the group consisting of antibiotics, antiinflammatories, antithrombotics, vitamins, peptide growth factors, nerve growth factors, and insulin like growth factors.

39. The method of claim 27, wherein the tissues are selected from a group consisting of blood vessels, gastrointestinal, genitourinary, reproductive, respiratory tubes, grafts, and synthetic prosthetics.

40. The method of claim 27, wherein at least one of the tissues expands when said insertable stent is introduced into said cavity.

41. The method of claim 27, wherein fusing is conducted without the use of an energy source which is extrinsic to the tissues.

42. The method of claim 27, wherein fusing comprises photothermal bonding.

43. The method of claim 27, wherein fusing comprises photochemical bonding.

44. The method of claim 27, wherein the insertable stent body comprises a radiopaque agent.

45. The method of claim 44, wherein said radiopaque agent is selected from the group consisting of iothalainate meglumine, diatrizoate meglumine, diatrizoate sodium, and ioversol.

46. An insertable stent for joining together and facilitating healing of adjacent tissues, each of the adjacent tissues defining an internal cavity, the insertable stent comprising:
an insertable stent body, formed of a protein, including at least one fusible portion and at least one unfusible portion, each said unfusible portion having a portion which is dissolvable during said healing; and
said unfusible portion of the insertable stent body permitting fluid to pass therethrough,
the insertable stent body being introduceable into, and fitting within the confines of the interal cavity, in contact with the adjacent tissues.

* * * * *

UNITED STATES PATENT AND TRADEMARK OFFICE
CERTIFICATE OF CORRECTION

PATENT NO. : 6,585,773 B1  Page 1 of 1
DATED : July 1, 2003
INVENTOR(S) : Xie

It is certified that error appears in the above-identified patent and that said Letters Patent is hereby corrected as shown below:

Column 1,
Line 55, "area The" should read -- area. The --.

Column 13,
Line 1, "method of claims 19" should read -- method of claim 19 --.
Line 48, "of alburins, elastins," should read -- of albumins, elastins --.

Column 14,
Line 37, "of iothalainate meglumine," should read -- of iothalamate meglumine, --.
Line 50, "the interal cavity," should read -- the internal cavity, --.

Signed and Sealed this

Fifteenth Day of June, 2004

JON W. DUDAS
*Acting Director of the United States Patent and Trademark Office*